United States Patent [19]

Raines

[11] 4,286,591

[45] Sep. 1, 1981

[54] SYRINGE CAP

[75] Inventor: Kenneth Raines, Bethlehem, Pa.

[73] Assignee: Burron Medical Inc., Bethlehem, Pa.

[21] Appl. No.: 163,694

[22] Filed: Jun. 27, 1980

[51] Int. Cl.³ .............................................. A61M 5/00
[52] U.S. Cl. ................................................... 128/215
[58] Field of Search .............. 128/215, 218 R, 218 P, 128/234, 260, 261, 220, 221

[56] References Cited

U.S. PATENT DOCUMENTS

| | | | |
|---|---|---|---|
| 3,344,786 | 10/1967 | Berg et al. ............................. | 128/215 |
| 3,674,181 | 7/1972 | Marks et al. ....................... | 128/218 P |
| 4,043,334 | 8/1977 | Brown et al. ........................ | 128/215 |

*Primary Examiner*—John D. Yasko
*Attorney, Agent, or Firm*—Shoemaker and Mattare, Ltd.

[57] ABSTRACT

A syringe cap includes a base which is polygonal in peripheral outline and has a planar top and a planar bottom. The cap is very stable in the upright orientation thereof and is easily grasped aseptically to be placed on or taken off of a syringe tip.

12 Claims, 4 Drawing Figures

SYRINGE CAP

BACKGROUND OF THE INVENTION

The present invention relates in general to syringes, and, more particularly, to syringe caps.

A pharmacist or doctor often fills a hypodermic syringe with the prescribed fluid, then stores that filled syringe.

The filled syringe is capped for storage, then a suitable needle is attached just prior to administering the fluid.

The cap used to close syringes should be easily attached and should be amenable to attachment without endangering the sterile field of the syringe.

There are several caps which have been used for this purpose. Examples of such caps are rubber or plastic caps and the like.

One cap is shown in U.S. Pat. No. 4,043,334, which as a bulbous rocker base. The protector cap disclosed in this patent is quite useful, but due to the bulbous shape of the base, the cap is not stable in the upright position thereof.

SUMMARY OF THE INVENTION

The protective cap embodying the teachings of the present invention is easily oriented in the upright position, and, once in such orientation, is quite stable.

The cap includes a weighted base which is in the form of one-half of a prolate elipse having flattened sides. The base is thinner than it is long and has a planar top and a planar bottom connected by arcuate sides. The base has a square peripheral shape in the preferred embodiment and is thus easily grasped without endangering the aseptic condition of a syringe attached to the cap via a tubular coupling element integrally attached to the base.

Arcuate wings are integrally located on the base to form guides on which the cap moves in an uprighting movement. The wings over hang the base to form finger holds.

The weighted base with rounded side panels permits the cap to right itself when subjected to a gentle shake or a gentle nudge. A user is thus permitted to insert a syringe tip into the bore of the coupling element without requiring use of two hands.

The square configuration of the base combined with the flat top and flat bottom of the base permits a cap to be "picked up", if desired, aseptically and twisted on or off the syringe tip.

The planar base bottom ensures that the cap will stably retain an upright orientation during attachment of that upright cap to a syringe.

OBJECTS OF THE INVENTION

It is a main object of the present invention to permit a user to insert a syringe tip into a protective cap without requiring such user to use two hands.

It is another object of the present invention to permit a syringe cap to be picked up aseptically and twisted on or off a syringe tip.

It is a further object of the present invention to stabilize a syringe cap during attachment thereof to a syringe.

These together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figure 1:
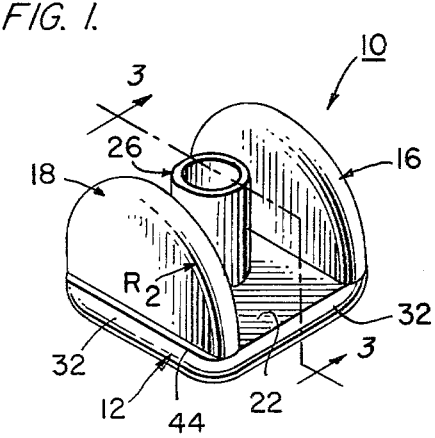
FIG. 1 is a perspective of a syringe cap embodying the teachings of the present invention.

Shown in FIG. 1 is a syringe cap 10 embodying the teachings of the present invention. The cap 10 is unitary and has a base 12 having a polygonal, preferably square, peripheral shape and a pair of upstanding wings 16 and 18 mounted on a planar mounting surface 22 of the base and can be in spaced parallelism with each other. A tubular syringe coupling 26 is mounted on the base surface 22 to extend upwardly therefrom.

Figure 3:
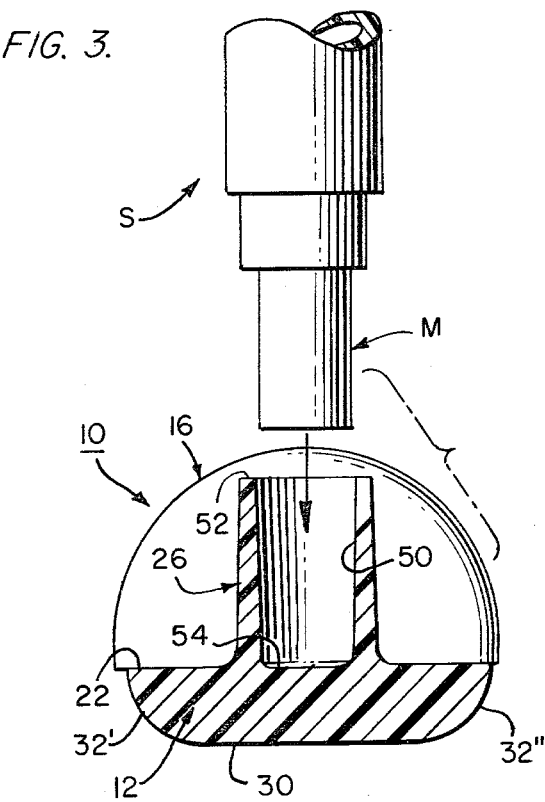
FIG. 3 is an elevation view of a syringe cap embodying the teachings of the present invention.

As best shown in FIG. 3, the base 12 includes a planar support surface 30 and arcuate side panels 32 which connect the support surface to the planar mounting surface 22. In the preferred embodiment, there are four arcuate side panels 32. In the position shown in FIG. 3, the side panels recede downwardly from surface 22 to surface 30. The base 12 is roughly in the shape of one-half of a prolate ellipse with flattened elongated sides. The thickness of the base as measured at the center thereof from surface 22 to surface 30 is less than the length of the base as measured between opposite side panels 32' and 32".

The above-described shape of the base permits the cap 10 to be maneuvered into a desired position, and, once in that position, to be quite stable during the attachment of s syringe thereto. The shape of the base also permits the cap to be easily turned into the orientation shown therefor in FIGS. 1 and 3. In fact, the FIGS. 1 and 3 position is the "desired" position for the cap as the cap seeks that position from all other positions upon being nudged or jostled. The base peripheral outline is preferably square, which permits that base to be easily grasped.

If the FIG. 1 position of cap 10 is considered the upright position, the cap 10 is thus a self-righting cap which moves easily into the upright position, and once in such position, is quite stable due to the shape of the base. The stable position of the base facilitates easy attachment and removal of a syringe from the cap. Because of the square shape of the base, the cap can be easily picked up and twisted off or on a syringe without danger of contaminating that syringe.

Figure 2:
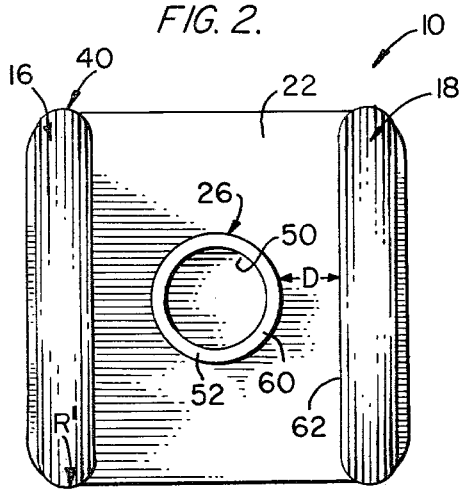
FIG. 2 is a plan view of a syringe cap embodying the teachings of the present invention.
Figure 4:
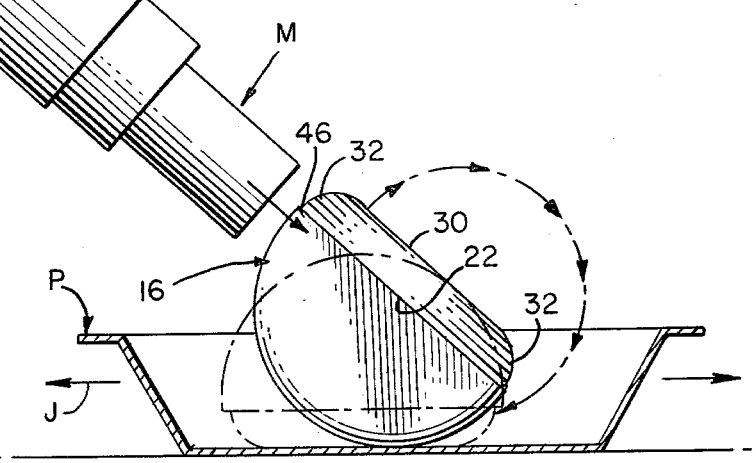
FIG. 4 is an elevation view showing a syringe cap embodying the teachings of the present invention being turned into an upright orientation using the tip of a syringe which is to be covered by that cap.

The wings 16 and 18 are best shown in FIGS. 1 and 2 to have arcuate rims 40 which are curved in two planes, that is, the rims are curved in arcs indicated by $R_1$ in FIG. 2 and in arcs indicated by $R_2$ in FIG. 1. The wings are identical and are located closely adjacent end edges 44 of the base mounting surface 22, but spaced therefrom to define a ledge 45. The ledge permits the cap to be easily picked up. The wings can be sloped slightly inwardly toward each other for a purpose which will be evident from the ensuing discussion. As best shown in FIGS. 3 and 4, the wings are slightly larger than the base to define overhangs 46 which form finger holds by which the cap 10 is easily grasped. As will be evident from the ensuing disclosure, the wings serve as guides on which the cap moves to assume the FIG. 1 position.

The tubular coupling 26 is best shown in FIGS. 1-3 and includes a blind-ended bore 50 which extends longitudinally of the coupling and which is tapered to converge from rim 52 to base 54 which closes the bore. The bore is tapered to snugly receive male tip M of a syringe S. Preferably, the coupling is intermediate the wings, but can be in other locations if suitable. The intermediate location of the coupling provides better balance to the cap than other locations. The coupling is integral with the base, as are the wings in the preferred embodiment.

As best shown in FIG. 3, the wings extend above the coupling 26 with respect to the surface 22 of the base. As will be evident from the ensuing disclosure, such relative sizes permits the cap to be easily oriented from an upset orientation to an upright orientation.

The cap 10 can rest on any surface, and can also be located in a package P as shown in FIG. 4. The package can be gently moved back and forth as indicated in FIG. 4 by arrows J to reorient the cap from the position shown in FIG. 4 in solid lines to a position shown in FIG. 4 in phantom lines. The syringe tip can also be used to nudge the cap into an upright orientation.

The bore 50 is preferably circular in transverse cross-section and tapered; however, other shapes, such as square, or the like, can be used without departing from the scope of the present disclosure. The bore need not be tapered if so desired.

As shown in FIG. 2, the distance D between outer surface 60 of the tubular coupling 26 and inner surface 62 of a wing is selected so that when a syringe tip is inserted into the coupling 26, the surfaces 60 and 62 come into contact with each other. This contact further enhances the snug nature of the fit between the tip and the cap, thereby enhancing the secure nature of the cap. The cap is thus protected against dislodgement from the syringe tip once engaged thereon.

It is also noted that the overhangs 46 enhance the rolling motion of the cap indicated in FIG. 4. There is no protusion to inhibit such rolling motion due to the overhangs 46.

The cap is preferably one-piece molded polypropylene, but the cap is not thus limited.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A syringe cap comprising:
   a base, said base having a polygonal peripheral shape, a planar top, a planar bottom, and arcuate sides connecting said planar top to said planar bottom;
   a pair of arcuate wing members mounted on said base top and extending upwardly therefrom; and
   a syringe tip coupling element mounted on said base top for releasably capping a syringe.

2. The syringe cap defined in claim 1 wherein said cap is unitary.

3. The syringe cap defined in claim 1 wherein said wings have rims curved in two planes.

4. The syringe cap defined in claim 1 wherein said wings extend over said base sides to define overhangs.

5. The syringe cap defined in claim 1 wherein said base is square.

6. The syringe cap defined in claim 1 wherein said coupling element is tubular and includes a blind-ended bore defined longitudinally thereof.

7. The syringe cap defined in claim 6 wherein said bore is tapered.

8. The syringe cap defined in claim 1 wherein said coupling element is located essentially intermediate said wings.

9. The syringe cap defined in claim 1 wherein said wing members are mounted adjacent the sides of said base.

10. The syringe cap defined in claim 1 wherein said wing elements extend above said coupling element with respect to said base.

11. The syringe cap defined in claim 1 wherein said base has a distance between said top and said bottom which is less than the distance between opposite ones of said arcuate sides.

12. The syringe cap defined in claim 1 wherein the distance between the coupling element and said wings is selected so that said wings contact said coupling element when a syringe tip is positioned in said coupling element.

* * * * *